US00PP32928P2

(12) United States Plant Patent
Bacon et al.

(10) Patent No.: US PP32,928 P2
(45) Date of Patent: Mar. 30, 2021

(54) PEACH TREE NAMED 'SUPECHTWENTYFIVE'

(50) Latin Name: *Prunus persica*
Varietal Denomination: Supechtwentyfive

(71) Applicant: Sun World International, LLC, Bakersfield, CA (US)

(72) Inventors: Terry A. Bacon, Bakersfield, CA (US); Terrence J. Frett, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 16/936,870

(22) Filed: Jul. 23, 2020

(51) Int. Cl.
*A01H 5/08* (2018.01)
*A01H 6/74* (2018.01)

(52) U.S. Cl.
USPC ..... Plt./197
CPC ..... *A01H 6/7463* (2018.05)

(58) Field of Classification Search
USPC ..... Plt./197
CPC ..... A01H 6/7463
See application file for complete search history.

*Primary Examiner* — Anne Marie Grunberg
(74) *Attorney, Agent, or Firm* — Knobbe, Martens, Olson & Bear, LLP

(57) ABSTRACT

A new and distinct variety of peach tree, *Prunus persica*, cv. 'Supechtwentyfive' is characterized by very early ripening, large-size fruit, with medium brix, melting flesh, strong adherence of the stone to the flesh, and a large percentage of over-color.

1 Drawing Sheet

Latin name of the genus and species claimed: *Prunus persica.*

Variety denomination: 'SUPECHTWENTYFIVE'.

BACKGROUND AND SUMMARY OF THE INVENTION

This invention relates to the discovery and asexual propagation of a new and distinct variety of peach, *Prunus persica* cv. 'Supechtwentyfive'. The variety 'Supechtwentyfive' was originated by hybridization and was first selected in May 2016 by Terry A. Bacon and Terrence J. Frett as breeder number: 'PE1813'. The new variety was first evaluated by Terry A. Bacon and Terrence J. Frett near Wasco, Calif. in Kern County.

The new variety 'Supechtwentyfive' is characterized by having very early ripening, large-size fruit, with medium brix, melting flesh, strong adherence of the stone to the flesh, and a large percentage of over-color.

The seed parent is 'Supechseventeen' (U.S. Plant Pat. No. 22,588), and the pollen parent is 'PeachLate12' (bulk pollen of unpatented breeding selections PE1363, PE1390, PE1391W, PE1404, and PE1405W). The parent varieties were first crossed in February 2012, with the date of sowing being February 2013, and the date of first flowering being February 2016. The new peach variety 'Supechtwentyfive' was first asexually propagated by Terry A. Bacon and Terrence J. Frett near Wasco, Kern County, Calif. in February 2017 by dormant grafting.

The new variety 'Supechtwentyfive' is distinguished from its seed parent, 'Supechseventeen', in that harvest of the fruit of the new variety starts about 5 days later than for 'Supechseventeen' and the percentage over-color of the new variety 'Supechtwentyfive' is higher at 100% compared to 85%+ for 'Supechseventeen'.

The fruit of the new variety 'Supechtwentyfive' has the same yellow flesh with some red color as 'Supechtwentyone' (U.S. Plant Pat. No. 26,773). However, the new variety 'Supechtwentyfive' ripens about 14 days earlier than 'Supechtwentyone'. Additionally, fruit of the new variety 'Supechtwentyfive' has a smaller fruit weight at 170 g compared to 200 g for the fruit of 'Supechtwentyone'.

The fruit of the new variety 'Supechtwentyfive' ripens about 6 days earlier than 'Supechtwentytwo' (U.S. Plant Pat. No. 30,979). Additionally, fruit of the new variety 'Supechtwentyfive' has a smaller fruit weight at 170 g compared to 180 g for the fruit of 'Supechtwentytwo'.

The fruit of the new variety 'Supechtwentyfive' ripens about 34 days earlier than 'Brittney Lane' (U.S. Plant Pat. No. 10,286). Additionally, the new variety 'Supechtwentyfive' has a smaller fruit weight at 170 g compared to 230 g for the fruit of 'Brittney Lane'.

The new variety 'Supechtwentyfive' has similar fruit size as 'Supechfifteen' (U.S. Plant Pat. No. 13,177). However, the new variety 'Supechtwentyfive' ripens about 7 days earlier than 'Supechfifteen' (U.S. Plant Pat. No. 13,177). Additionally, the fruit of the new variety 'Supechtwentyfive' has higher degree of overcolor at 100% compared to 80%+ for 'Supechfifteen'. The fruit of the new variety 'Supechtwentyfive' has a higher brix at 13% compared to 11% for 'Supechfifteen'

The new variety 'Supechtwentyfive' has been shown to maintain its distinguishing characteristics through successive asexual propagations by, for example, cuttings and grafting.

DETAILED DESCRIPTION OF THE PREFERRED EMBODIMENT

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England, 1986.

The descriptive matter which follows pertains to 4-year-old 'Supechtwentyfive' trees grown in the vicinity of Wasco, Kern County, Calif., during 2020, and is believed to apply to plants of the variety grown under similar conditions of soil and climate elsewhere.

TREE

General: (Measurements taken on 4-year-old trees unless otherwise noted.).

*Size*.—Medium. Reaches a height of approximately 3 meters with normal pruning.

*Vigor*.—Strong. Top shoot growth of about 1.5 meters during the first growing season.

*Growth*.—Semi-upright.

*Productivity*.—Very Productive.

*Fertility*.—Self-fertile.

*Hardiness*.—Hardy in all fruit growing areas of California; winter chilling requirement is approximately 200 hours at or below 7.2° C.

*Disease resistance/susceptibility*.—No specific testing for relative plant disease resistance/susceptibility has been undertaken. Under close observation in Kern County, Calif., no particular plant/fruit disease resistance/susceptibility has been observed.

Trunk: (Measurements taken at approximately 30 cm above the soil line.).

*Diameter*.—Approximately 16 cm.

*Texture*.—Medium shaggy, increases with the age of the tree.

*Trunk color*.—About Light Grey 198D with highlights of Medium Greyed-Red 182B, becoming darker with age.

Branches: (Measurements taken at approximately 90 cm above the soil line.).

*Size*.—Approximately 12 cm.

*Texture*.—Medium shaggy; increasing with tree age.

*Color*.—About Light Grey 201D with highlights of Medium Greyed-Red 182B, becoming darker with age.

*Lenticels density*.—Plentiful, approximately 1-3 per $cm^2$.

*Lenticels color*.—About Light Grey 201D.

*Lenticels length*.—Approximately 5 mm.

*Lenticels width*.—Approximately 1.2 mm.

One year old shoots: (Data taken in May at midpoint of current-season growth.).

*Size*.—Average diameter approximately 5 mm.

*Color*.—Topside: About Medium Yellow-Green 146C Underside: About Medium Yellow-Green 146C.

*Internode length*.—Medium; approximately 2-3 cm.

*Lenticels and density*.—Plentiful; about 8 per $cm^2$.

*Color*.—About Light Grey 201D.

*Lenticel dimensions*.—Width: Approximately 0.2 mm. Length: Approximately 1 mm.

*Presence of anthocyanin coloration*.—Absent or very sparse.

*Density of flower buds*.—Medium, two per node.

FOLIAGE

Leaves: (Data taken in May on fully expanded leaves at midpoint of current-season growth).

*Average length*.—Medium; approximately 16 cm without petiole.

*Average width*.—Medium; approximately 4.1 cm.

*Length*.—Width ratio: Medium; about 4.4:1.

*Shape*.—Elliptic.

*Color*.—Upper Surface: About Dark Green 139A. Lower Surface: About Medium Green 138B.

*Angle at base*.—Acute.

*Angle at apex*.—Acute, small.

*Vein color*.—About Light Green 139D.

*Presence of red coloration of mid-vein on the lower side*.—Absent or very sparse.

*Surface texture*.—Smooth on both top and bottom surfaces.

*Shape in the cross section*.—Flat.

*Leaf blade tip*.—Curved downwardly.

*Undulation of margin*.—Slight.

*Margin*.—Crenate.

Petiole:

*Average length*.—Short; approximately 4 mm.

*Average diameter*.—Approximately 2 mm.

*Color*.—About Medium Green 139C.

Stipules:

*Number/leaf bud*.—Usually 2.

*Typical length*.—Medium; approximately 11 mm.

*Color*.—About Dark Greyed-Orange 166A when dried.

*Persistence*.—Falls off.

Leaf glands (nectaries):

*Form*.—Reniform.

*Average number and arrangement*.—Usually 0-4, alternating. Predominately on petiole.

*Dimension*.—Approximately 1 mm long by 0.8 mm wide.

*Color*.—About Dark Greyed-Yellow 162A, becoming Dark Greyed-Orange 166A over time.

Vegetative buds (Data taken in September at midpoint of current-season growth):

*Bud dimensions*.—Approximately 5 mm long by 2.5 mm wide.

*Bud shape*.—Conical.

*Color*.—About Dark Greyed-Orange 177A.

Flower buds:

*Bud dimensions*.—Approximately 3 mm long by 2 mm wide.

*Bud shape*.—Ovoid.

*Color*.—About Dark Greyed-Orange 177A.

*Ratio of flower buds to vegetative buds*.—2 flower buds:1 vegetative bud.

FLOWERS

General:

*Type of bloom*.—Showy.

*Diameter of fully opened flower*.—Approximately 28 mm.

*Flower aroma*.—Slight aroma.

*Time of beginning of leaf bud burst*.—Early, with bloom.

*Flower blooming period*.—First Bloom: Approximately February 6. Full Bloom: Approximately February 10.
*Time of bloom*.—Early.
*Location of first bloom*.—Tips of one-year-old shoots.
*Location of full bloom*.—Central part of the tree canopy.
*Duration of bloom*.—Approximately 10 days.

Pedicels:
*Dimensions*.—Approximately 3 mm long by 2 mm wide.
*Color*.—About Medium Green 138B.

Sepals:
*Number*.—5.
*Shape*.—Medium ovate.
*Position*.—Adpressed to petals.
*Length*.—Approximately 5 mm.
*Width*.—Approximately 3 mm.
*Surface texture*.—Smooth.
*Color*.—About Dark Greyed-Purple 184A.

Petals:
*Number*.—5.
*Arrangement*.—Touching.
*Color*.—About Light Pink 54D.
*Surface texture*.—Smooth.
*Dimensions*.—Approximately 13 mm long by 7 mm wide.
*Shape*.—Narrow elliptic.
*Apex shape*.—Rounded.
*Base shape*.—Narrows at point of attachment.
*Undulation of margins*.—Medium.
*Width*.—Medium, approximately 7 mm.
*Frequency of flowers with double petals*.—Never.
*Claw*.—Partially developed.

Stigma:
*Position compared to anthers*.—Above.

Stamens:
*Number*.—About 40.
*Length*.—Variable, ranging from 7 mm to 10 mm.
*Filament color*.—About White 155A with highlights of Light Pink 54D.
*Pollen*.—Present.
*Flower pollen color*.—About Medium Greyed-Orange 166C.
*Position compared to petals*.—At the same level.

Anthers:
*Pollen*.—Present.

Pistil:
*Length*.—Approximately 17 mm.
*Ovary diameter*.—Approximately 2 mm.
*Frequency of supplementary pistils*.—Few.

Receptacle:
*Depth*.—Medium, about 4 mm.
*Pubescence of inner surface* (*at pink bud stage*).—Absent.
*Pubescence of outer surface*.—Present.

Ovary:
*Pubescence*.—Present.

FRUIT

General: (Description taken at firm-mature near Wasco, Kern County, Calif.).
*Date of first pick*.—Approximately April 27.
*Date of last pick*.—Approximately May 7
*Time of maturity for consumption*.—Very early.

Peduncle:
*Dimensions*.—Approximately 7 mm long by 3 mm wide.
*Color*.—About Light Green 139D.

Fruit size:
*Size*.—Large; about 170 g.
*Height*.—Tall; about 70 mm.
*Diameter perpendicular to suture*.—Approximately 74 mm.
*Diameter ventral side, facing suture*.—Approximately 74 mm.

Fruit shape:
*Shape viewed from apex*.—Circular.
*Shape in lateral view, perpendicular to suture*.—Circular.
*Shape ventral side, facing suture*.—Circular.
*Symmetry viewed from pistil end*.—Symmetric or slightly asymmetric.
*Shape of pistil end*.—Weakly pointed.
*Mucron tip at pistil end*.—Occasionally present.
*Depth of stalk cavity*.—Medium; about 7 mm.
*Width of stalk cavity*.—Medium; about 7 mm.
*Promenence of suture*.—Weak or flat.

Fruit skin:
*Thickness*.—Medium.
*Adherence to flesh*.—Strong.
*Taste*.—Neutral.
*Surface texture*.—Smooth.
*Reticulation*.—Absent.
*Tendency to crack*.—None.
*Pubescence*.—Slight.
*Density of pubescence of skin*.—Medium.
*Ground color*.—About Medium Yellow-Orange 16B.
*Relative area of overcolor*.—About 100%.
*Overcolor color* (*hue*) *of skin*.—About Medium Red 46B to Dark Red 46A.
*Pattern of overcolor of skin*.—Solid flush.

Flesh:
*Ripens*.—Evenly.
*Color*.—About Medium Yellow 14C.
*Anthocyanin coloration of flesh next to skin*.—Weak.
*Anthocyanin coloration of flesh in central part of flesh*.—Weak.
*Anthocyanin coloration of flesh around stone*.—Absent.
*Flavor*.—Sweet mild.
*Firmness*.—Firm; typically 101b pressure at harvest.
*Juice*.—Medium; able to squeeze free juice easily.
*Acidity*.—Medium; 0.80% titratable.
*Sweetness*.—Medium; about 13% brix at harvest.
*Flesh type*.—Melting.
*Amount of fiber*.—Moderate.

Stone:
*Stone size*.—Medium. Size compared to Fruit: Medium. Length: Approximately 32 mm. Diameter Facing Suture: Approximately 22 mm. Diameter Perpendicular to Suture Plane: Approximately 27 mm.
*Stone color*.—About Medium Greyed-Yellow 161B when dried.
*Anthocyanin color*.—Absent.
*Intensity of brown color*.—Light.
*Position of maximum*.—Middle.

*Shape in lateral view perpendicular to suture*.—Circular.

*Shape in ventral view facing suture*.—Medium elliptic.

*Shape in basal view*.—Medium elliptic.

*Base shape*.—Nearly straight.

*Apex shape*.—Slight point at tip.

*Ridges*.—Rounded throughout.

*Outgrowing keel*.—Partially developed.

*Fibers*.—Not visible.

*Symmetry in lateral view*.—Symmetric or slightly asymmetric.

*Relief of surface*.—Predominately pits.

*Width of stalk end*.—Narrow.

*Tendency to split*.—Low.

*Degree of adherence to flesh*.—Strong.

What is claimed is:

1. A new and distinct variety of peach tree as herein described and illustrated.

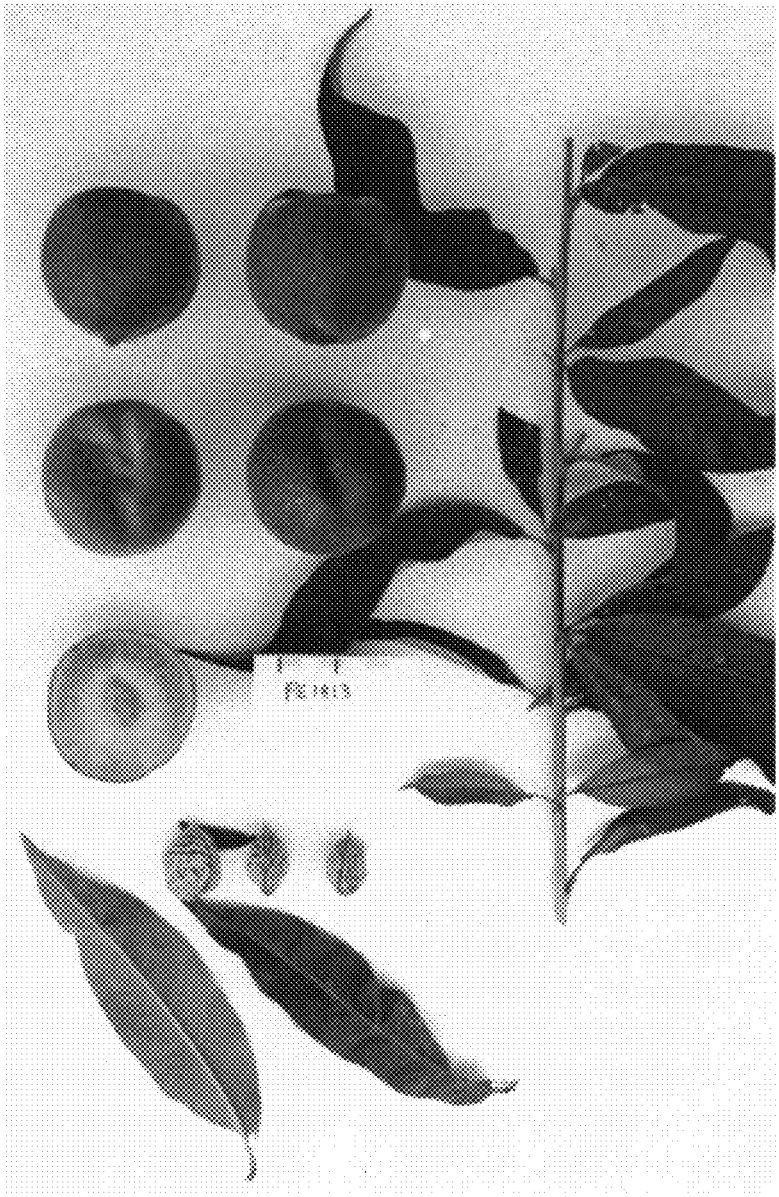

* * * * *